United States Patent [19]

Banerjee et al.

[11] Patent Number: 5,013,654
[45] Date of Patent: May 7, 1991

[54] PRODUCTION OF EMULSIFYING AGENTS AND SURFACTANTS

[75] Inventors: Santimoy Banerjee, Chicago, Ill.; Jeffrey S. Karns, Greenbelt, Md.; Ananda M. Chakrabarty, Villa Park, Ill.

[73] Assignee: The Board of Trustees of the University of Illinois, Urbana, Ill.

[21] Appl. No.: 490,548

[22] Filed: Mar. 5, 1990

Related U.S. Application Data

[63] Continuation of Ser. No. 158,105, Feb. 16, 1988, abandoned, Continuation of Ser. No. 600,972, Apr. 16, 1984, abandoned.

[51] Int. Cl.$^5$ .................. C12P 19/00; C12N 1/20
[52] U.S. Cl. .................. 435/72; 435/101; 435/102; 435/104; 435/253.3; 435/875; 536/55.1; 536/123
[58] Field of Search .............. 435/72, 101, 102, 104, 435/253.3, 875; 536/55.1, 123

[56] References Cited

U.S. PATENT DOCUMENTS 3,843,517 10/1974 McKinney et al. .................. 210/611

FOREIGN PATENT DOCUMENTS 2150375 4/1972 Fed. Rep. of Germany ........ 435/72

OTHER PUBLICATIONS

Hisatsuka et al., "Protein produced by Pseudomonas", CAS, vol. 82, 153788f.
Hisatsuka et al., "Formation of rhamnolipid by Pseudomanas aeruginosa and its function", CAS, vol. 75:62168t.
Bergey's Manual of Determinative Bacteriology, 8th Ed., Pseudomanaceae, pp. 219–222.
Clark, Jr. et al., Experimental Biochemistry, 2nd Ed., 1977, p. 175.
Houston, C. W., Biological Degradation of Hydrocarbons in Water, CA 82:40532z.
Vlasova et al., Susceptibility of Petroleum Distillate Fuels to Biodegradation, CA 98:200962a.
Hisatsuka et al., Agr. Biol. Chem., 1971, 35(5), pp. 684–690.
Itoh, J. Antibiotics, vol. 24, No. 12, pp. 855–899 (1971).
Hirayama et al., FEBS Letters, vol. 139, No. 1, 3/1982, pp. 81–85.
Jarvis et al., JACS, 71, pp. 4124–4126 (1949).
Goto, Japan J Microbiol., vol. 17(1), pp. 45–51 (1973).
Olsen et al., Unitar Conference on Heavy Oil Recover, 7/22–31, 1985.
Guerra–Santos et al., Third European Congress on Biotechnology, vol. 1, pp. I-506-513.
Syldatk et al., Z. Naturforsch (1985), 40, 1-2, 51–60.
Wagner et al., Third European Congress on Biotechnology, 9/10–14, 1984.
Hauser et al., J. Bacteriol., 68:645–654 (1954).
Evans et al., J. Bacteriol., 116(2), pp. 915–924 (1973).
Burger et al., Methods of Enzymology, 78, 441 (1966).

Primary Examiner—Carolyn S. Elmore
Attorney, Agent, or Firm—Marshall, O'Toole, Gerstein, Murray & Bicknell

[57] ABSTRACT

A novel strain of *Pseudomonas aeruginosa*, designated as strain SB-1, is capable of growth on hydrocarbon substrates having 10 to 32 or more carbon atoms, during which growth there is secreted into the culture medium an emulsifier which can be recovered and used for such applications as reducing the viscosity of crude oil in secondary recovery methods, as well as in oil spill management and the cleaning of oil-contaminated vessels and pipelines. A novel mutant strain of *P. aeruginosa* SB-1, designated SB-3, has the property of growing on solid ($C_{20}+$) paraffins but not on liquid alkanes. The selective degradation by strain SB-3 of the solid paraffinic components in crude oil is advantageous in reducing the viscosity of the oil for improving the recovery thereof from oil wells. A novel revertant strain of *P. aeruginosa* SB-3, designated SB-30, grows both on liquid and solid hydrocarbon substrates, but produces greater amounts of emulsifier than are produced by SB-1 when grown on other relatively inexpensive sources of carbon, such as corn oil or chicken fat.

4 Claims, 7 Drawing Sheets

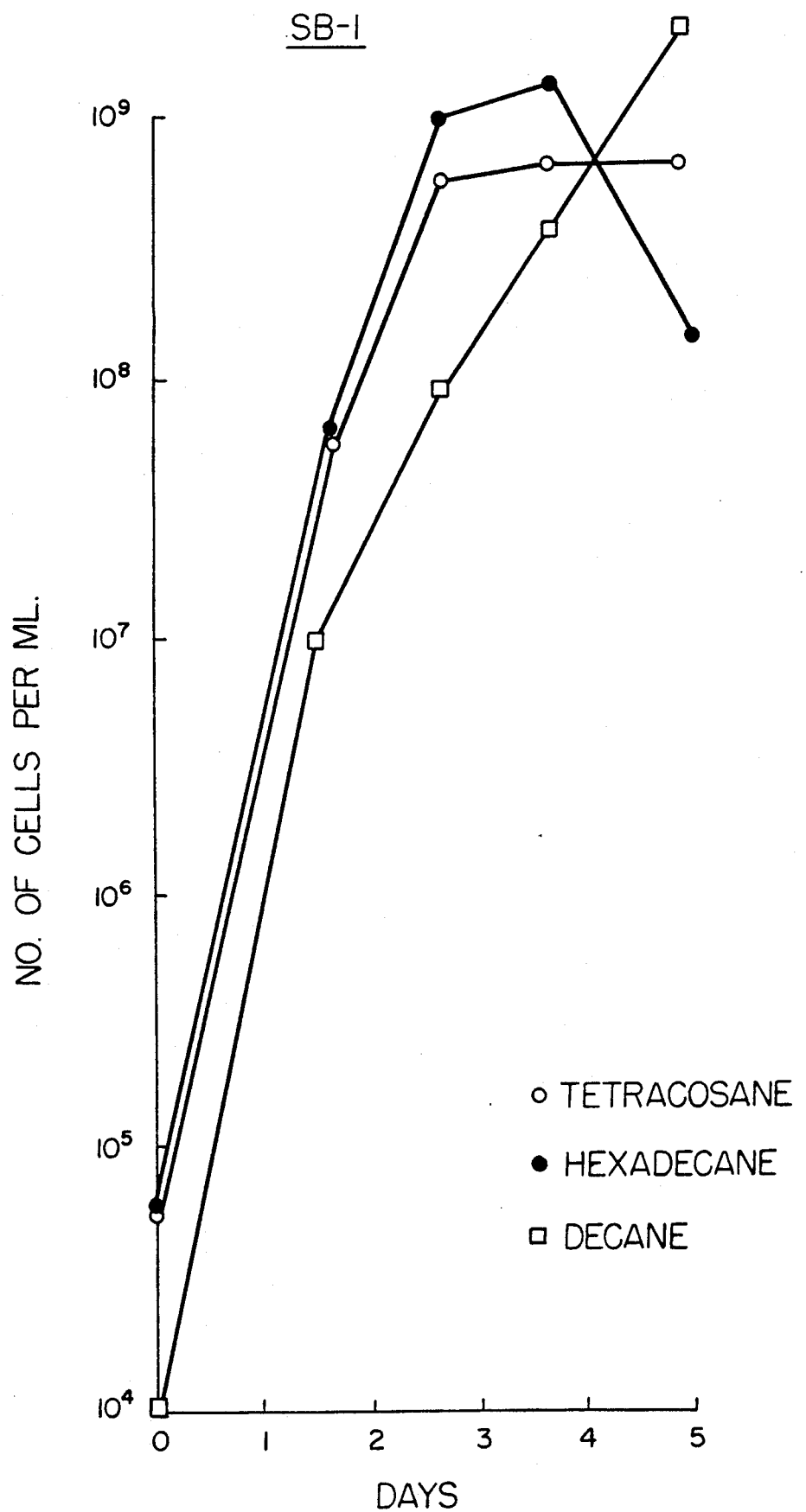

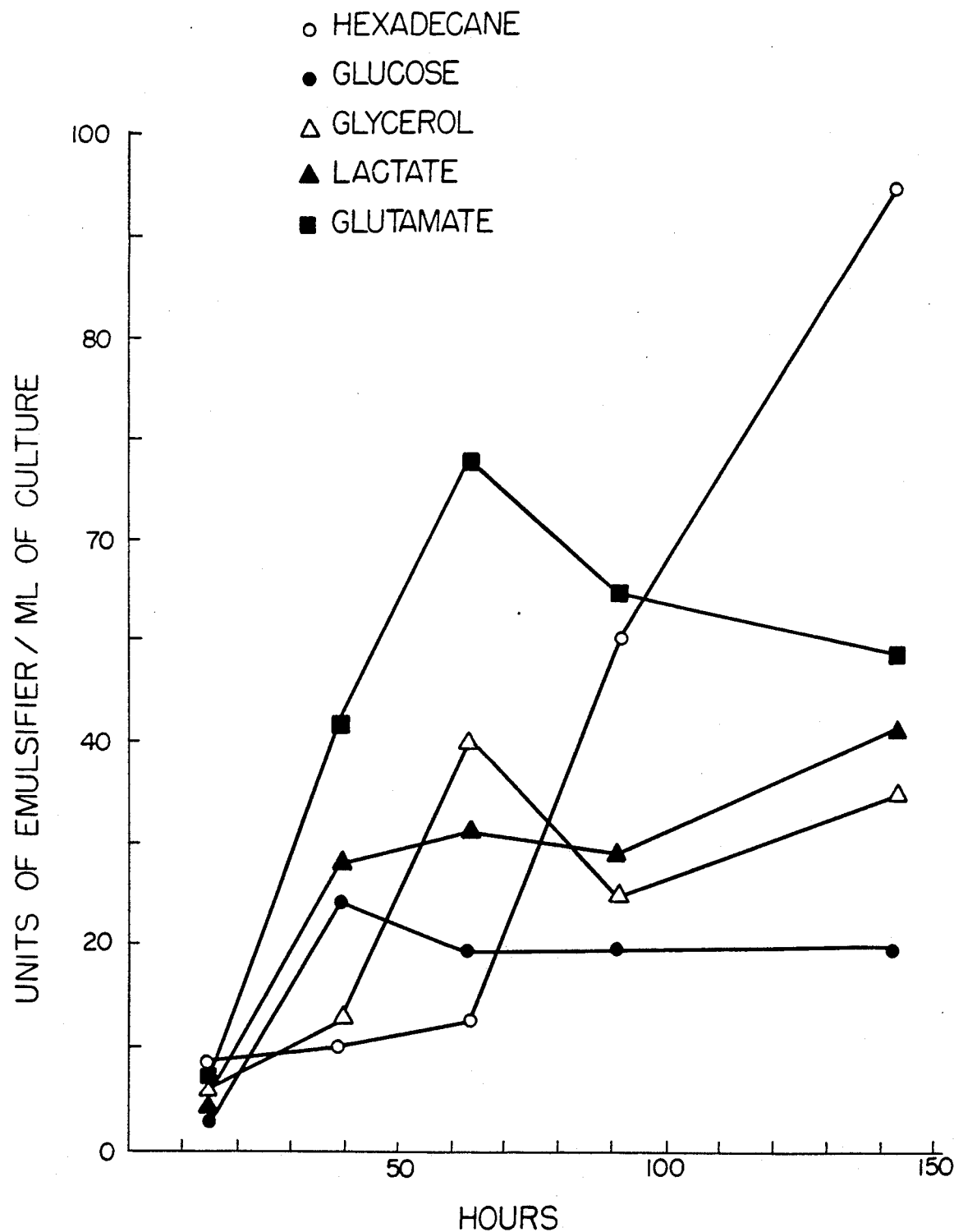

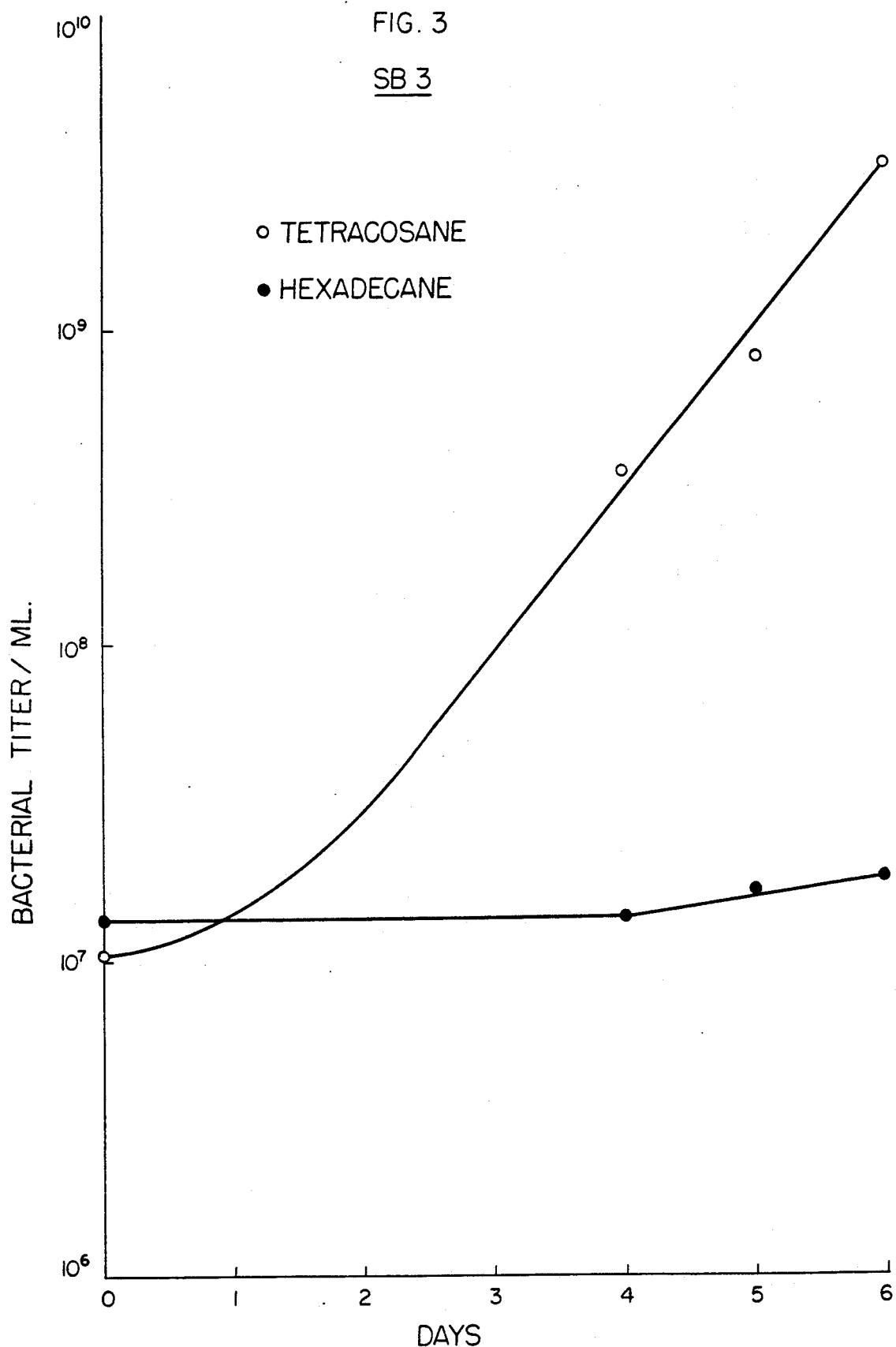

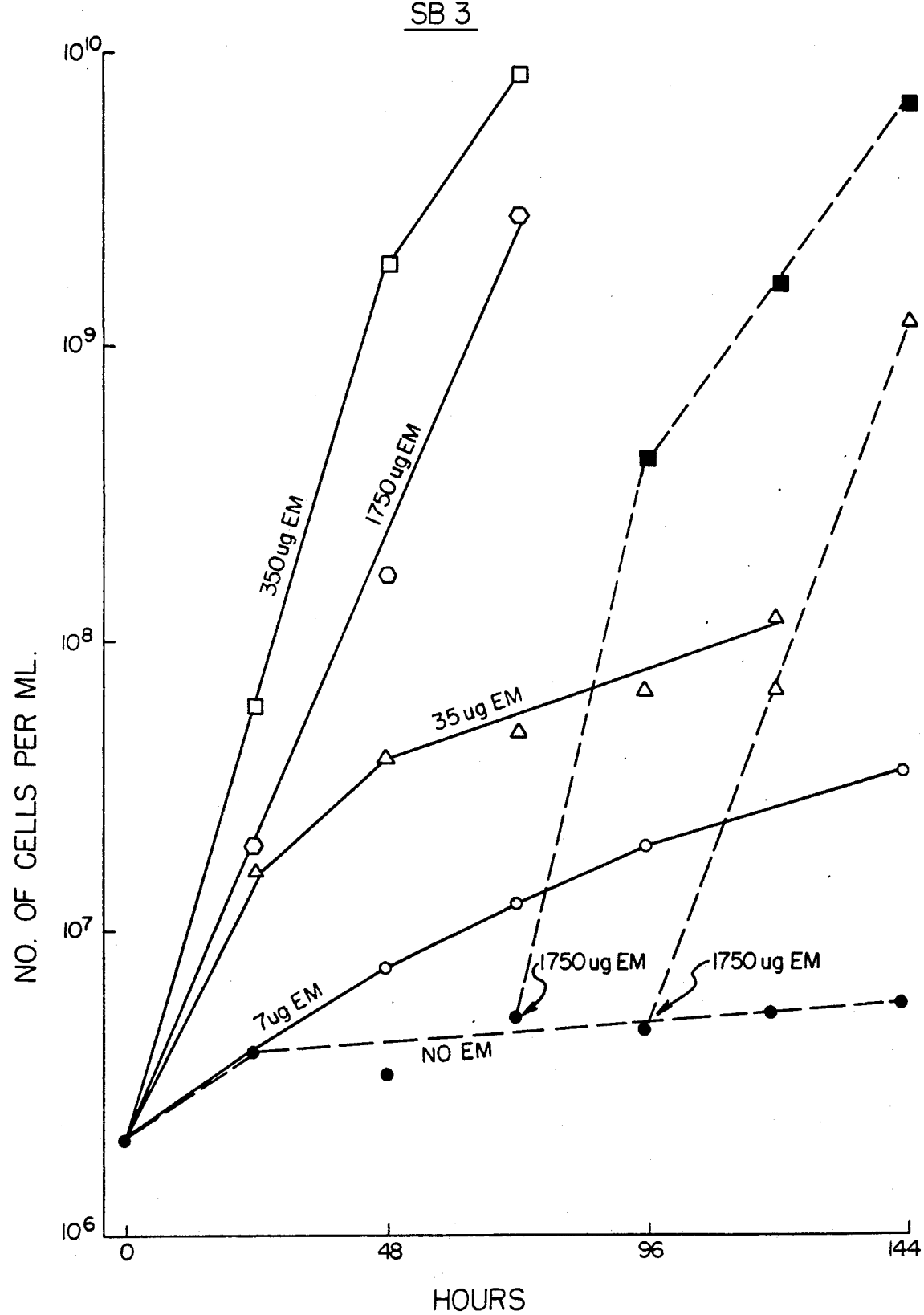

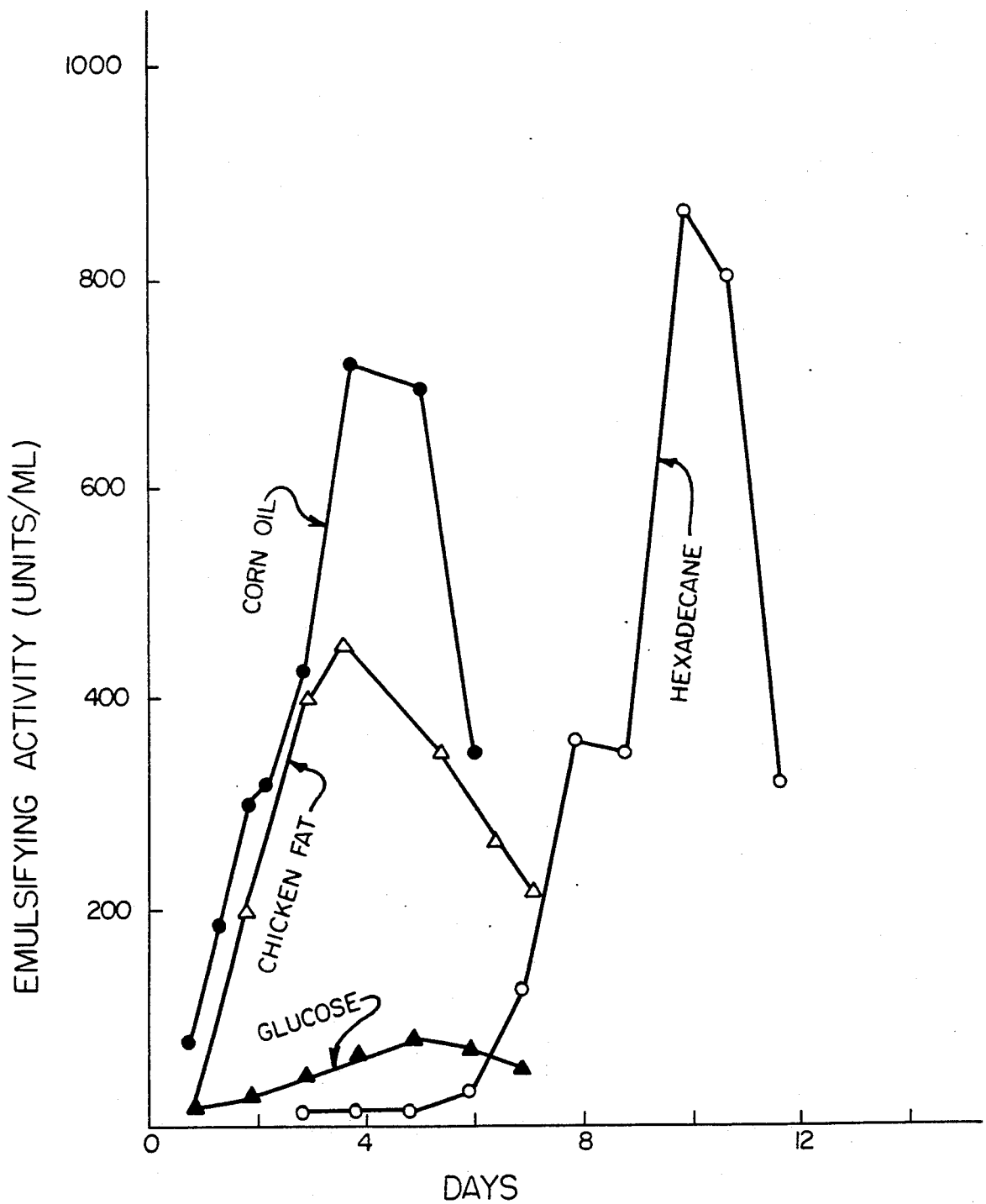

5,013,654

PRODUCTION OF EMULSIFYING AGENTS AND SURFACTANTS

This application is a continuation of application Ser. No. 07/158,105, filed 2/16/88 which is a continuation application of Ser. No. 06/600,972 filed 4/16/84, now abandoned.

The present invention relates to certain novel strains of *Pseuodomonas aeruginosa* capable of growing on paraffins as the sole source of carbon and energy, to an emulsifier produced by the bacteria which has valuable emulsifying and surfactant properties, and to a mutant strain of *P.aeruginosa* which degrades solid but not liquid paraffins.

BACKGROUND OF THE INVENTION

It is known that certain microorganisms which grow on hydrocarbons produce and emit into the culture medium compounds having emulsifying properties, known as bio-emulsifiers. Such emulsifiers can be highly effective for producing oil-in-water emulsions with a variety of crude oils and petroleum fractions, so that the emulsifiers are useful for such applications as cleaning storage tanks, drums or barrels, tank cars, tankers, barges, pipelines and the like; for cleaning oil spills; and for enhanced recovery of oil from oil wells. Bio-emulsifiers produced in this manner are biodegradable, so that their use presents no pollution problems.

It is estimated that as much as two-thirds of the crude oil in an oil field cannot be recovered by conventional means because of the high viscosity of the oil. Crude oil is a complex mixture of paraffinic and aromatic hydrocarbons together with small quantities of oxygen, nitrogen and sulphur-containing compounds. As the proportion of higher hydrocarbons in the oil increases, its viscosity increases, thus increasingly impeding the flow of the oil through the pores of the oil-bearing rock formations.

Recent trends in methods for microbial enhanced oil recovery (MEOR) comprise the injection of certain microorganisms into the oil well. Although the practice has been to employ anaerobic bacteria for such purposes, it is assumed that use of hydrocarbon degrading aerobic bacteria would be much more effective, provided air under pressure can be injected together with the bacteria. The beneficial effects of such aerobic cultures arise from two sources: (1) the ability of the microorganism to degrade higher hydrocarbons, thereby reducing the viscosity of the oil; and (2) production by the microorganism of an emulsifier which leads to the production of an oil-in-water emulsion having a lower viscosity than that of the unemulsified oil.

The production of emulsfer during the growth on hydrocarbon substrates of certain strains of bacteria is known, e.g., *Arthrobacter RAG*-1 (Rosenberg et al., Applied Environmental Microbiology, March, 1979, pp. 402–408). *Corynebacterium lepus* (Cooper et al., Applied Environmental Microbiology, January, 1979, pp. 4–10); and *Pseudomonas aeruginosa* $S_7B_1$ (Hisatsuka et al., *Agr. Biol. Chem.*, Vol. 35, No. 5, pp. 686–692, 1971). The use of such organisms for reducing the viscosity of crude oil for enhanced secondary recovery has also been reported (Singer, et al., *International Conferences on Microbiological Enhancement of Oil Recovery. Proc. of* 1982, May 16, 1982, pp. 94–101).

Gutnick et al. U.S. Pat. Nos. 4,311,829, 4,311,830, 4,311,831 and 4,311,832 disclose emulsifiers produced by *Acinetobacter Sp.*, A.T.C.C. No. 31012 (RAG-1) and the use of such emulsifiers in secondary recovery methods, for cleaning oil contaminated vessels, and in oil spill management.

SUMMARY OF THE INVENTION

In accordance with the invention, there is provided a strain of *Pseudomonas aeruginosa*, designated herein as strain SB-1, which is capable of growth on hydrocarbon substrates having 10 to 32 or more carbon atoms, during which growth there is secreted into the culture medium an emulsifier which can be recovered and used for such applications as reducing the viscosity of crude oil in secondary recovery methods, as well as in oil spill management and the cleaning of oil-contaminated vessels and pipelines. The invention also provides a novel mutant strain of *P.aeruginosa* SB-1, designated SB-3, which has the property of growing on solid ($C_{20}+$) paraffins but not on liquid alkanes. The selective degradation by strain SB-3 of the solid paraffinic components in crude oil is advantageous in reducing the viscosity of the oil for improving the recovery thereof from oil wells. A novel revertant strain of *P.aeruginosa* SB-3. designated SB-30, grows both on liquid and solid hydrocarbon substrates, but produces greater amounts of emulsilfier than are produced by SB-1 when grown on other relatively inexpensive sources of carbon, such as corn oil or chicken fat.

DESCRIPTION OF THE DRAWINGS

FIG. 1 is a graph depicting the growth of *P.aeruginosa* SB-1 on several different paraffinic sources of carbon;

FIG. 2 is a graph depicting the production of emulsifier during the growth of strain SB-1 on several different substrates;

FIG. 3 is a graph depicting the qrowth of mutant strain *P.aeruginosa* SB-3 on liquid (hexadecane) and solid (tetracosane) hydrocarbon substrates;

FIG. 4 is a graph showing the effect of the presence of the emulsifler produced by strain SB-1 on the ability of strain SB-3 to grow on a hexadecane substrate;

FIG. 6 is a graph showing the production of emulsifier by strain SB-30 grown on several different substrates.

DETAILED DESCRIPTION

Production of *P.aeruginosa* SB-1

Figure 5A:
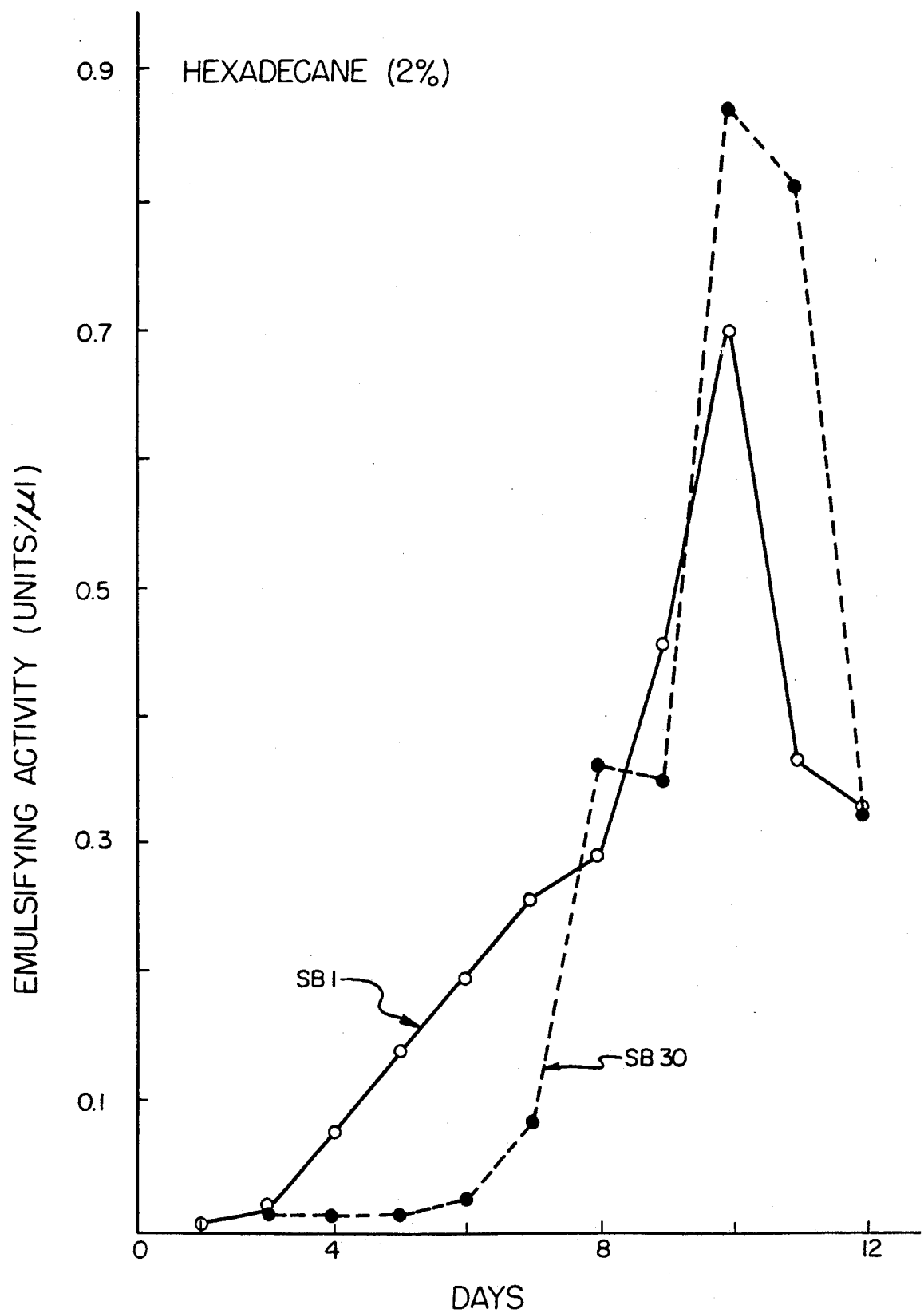
FIGS. 5a–5c are graphs depicting the production of emulsifier during the growth of strains SB-1 and SB-30 on different carbon sources (hexadecane, glucose, and chicken fat, respectively)

In accordance with the invention, there is provided a strain of *P.aeruginosa*, designated SB-1, which was isolated from oil-contaminated soil samples. A culture of the organism has been deposited without restrictions in the American Type Culture Collection, Washington, D.C., as strain No. A.T.C.C. 39617. The organism was isolated in the following manner.

A plasmid-assisted molecular breeding technique (Kellogg et al., Science, Vol. 214, pp. 1133–1136) was employed to isolate a strain of bacteria which could metabolize and grow on solid paraffins as its sole source of carbon and energy. A chemostat was set up with saturated paraffins recovered from oil-well operations as the major carbon source. Samples of soil collected from oil-contaminated areas in Texas and Illinois were grown overnight in Luria broth and the cells were added to the chemostat. A stream of air was continuously bubbled into the chemostat culture, which was also continuously stirred and replenished with basal salts medium (BSM). After about 2 months, an aliquot from this chemostat was inoculated into a second chemostat containing pure dotriacontane ($C_{32}H_{66}$) as the source of carbon. After about 2 weeks, the culture from the second chemostat was streaked out on L-agar plates for single colonies. Five types of colonies were found. They were separately inoculated into flask cultures containing dotriacontane. One of the colonies grew and was further purified on L-agar plates. The pure strain was identified as *Pseudomonas aeruginosa* and designated strain SB-1.

FIG. 1 shows the kinetics of growth of SB-1 in minimal salts medium containing 3 different hydrocarbons as its sole source of carbon. The data represented by this Figure were obtained as follows. SB-1 cells were grown overnight in Luria broth from a single colony. After washing and resuspension in BSM, 0.1 ml of the wash cells was added to 100 ml of BSM containing sterilized decane (1% by volume), hexadecane (1% by volume), or tetracosane (1 mg/ml). At the indicated times, an aliquot was diluted and plated in L-agar plate to determine the number of viable cells.

In addition to the substrates depicted in FIG. 1, SB-1 also grows well with other common carbon sources such as glucose, glycerol, lactate, and glutamate, as shown in FIG. 2, but does not grow on hexane or octane. The ability of SB-1 to grow in paraffins is stable even after 6 passages through L-broth. SB-1 can grow at temperatures up to 42° C. in minimal glucose or hexadecane medium and can tolerate sodium chloride concentrations of up to 1% when growing in minimal medium or up to 2.5% when growing in L-broth.

Production of *P.aeruginosa* SB-3

*P.aeruginosa* SB-1 produces an emulsifier when grown on hydrocarbon substrates. When injected into an oil well, the emulsifier produced by such growth would be beneficial in reducing the viscosity of the oil. In addition, the strain itself can reduce the viscocity of the oil further by degrading the waxy paraffinic components. The simultaneous degradation of the liquid hydrocarbons, however, presents a possible disadvantage in the that the liquid fractions of the oil may also be degraded. More desirable would be an organism which grows solely on the higher molecular weight, normally solid, paraffinic constituents, resulting in a decrease in the viscosity of the oil without affecting the quality or the amount of the liquid fractions.

An organism capable of growing on solid ($C_{20}+$) paraffins, but not on normally liquid paraffins, has been produced in accordance with the invention by mutagenesis of *P.aeruginosa* SB-1. A culture of the mutant, designated *P.aeruginosa* SB-3, has been deposited in the American Type Culture Collection, Washington, D.C., as A.T.C.C. 39616.

SB-3 was isolated by ethyl methane sulphonate (EMS) mutaqenesis of SB-1 followed by carbenicillin and cycloserine killing of the non-mutants. An overnight grown culture of SB-1 was diluted 100 fold in L-broth grown at 30° for 2 hours. The log phase cells were centrifuged and resuspended in basal salt medium (BSM, half volume). To 2.5 ml of the suspension was added 25 μl of EMS and the culture was shaken at 30° C. for 1 hour. The cells were centrifuged, washed twice with 0.9% sterile saline, resuspended in 10 ml Luria broth (LB) and grown overnight at 30°. 5 ml of culture was centrifuged, the cells were washed twice with saline and resuspended in BSM. 0.5% of suspension was diluted in 10 ml of BSM containing hexadecane (1%) and decane (1%). After 3 hours of shaking at 30°, carbenicillin (2 mg/ml) and cycloserine (100 μg/ml) was added and the culture was shaken for 3 days at 30°. The cells were then centrifuged, washed, resuspended in LB and grown overnight at 30°. An aliquot of this culture was again subjected to carbenicillin and cycloserine killing and the cycle was repeated four times, after which cells grown in LB were plated out at proper dilution to get 50–100 colonies per plate (L-agar). The colonies were then replicated onto hexadecane-BSM and L-agar plates. A few mutants were isolated. Most of them, when checked for growth in liquid culture, started to grow in hexadecane (representative of liquid paraffins) after 2–3 days. One mutant, designated SB-3, did not grow in hexadecane over a period of 6 days, but grew in tetracosane during that period, as shown in FIG. 3. SB-3 was similarly found to be unable to grow on dodecane, tetradecane, or any other normally liquid alkane.

The inability of strain SB-3 to grow on liquid paraffins is due to its failure to produce an emulsifier, such as that produced by SB-1, which is necessary for such growth. As shown in FIG. 4, SB-3 in minimum medium did not grow in 6 days with hexadecane as a carbon source but did so when a crude preparation of emulsifier produced by strain SB-1 was added to the medium either initially or after a period of time. At limiting emulsifier concentration, the growth rate was slow. As the concentration of the emulsifier in the medium was increased, the rate of growth also increased. As in the case of hexadecane, SB-3 could grow on other liquid hydrocarbons such as tetradecane or dodecane when the emulsifier is added to the growth medium. Addition of emulsifier alone in the absence of hexadecane did not allow any growth. It is evident therefore that emulsifier is necessary for growth of SB-3 cells on liquid hydrocarbons but not for growth with higher-chain solid paraffins.

Production of *P.aeruginosa* SB-30

Although SB-3 does not grow on liquid paraffins in the absence of emulsifier, it was found that after extensive incubation in the presence of hexadecane, SB-3 reverted to a strain which produced emulsifier and thus permitted the growth of the organism on both solid and liquid paraffins having at least 12 carbon atoms. The revertant strain of SB-3, however, could not grow on decane.

A pure culture of the revertant strain, designated as SB-30, was isolated as follows. SB-3, the mutant of SB-1 which does not produce emulsifier and does not grow in hexadecane, was inoculated into 100 ml of BSM-hexadecane medium in a 500 ml flask and incubated with shaking at 30° C. After one week the culture started to grow, and after 2 weeks, it was plated out at proper dilution on L-agar plates for single colonies. From these colonies, one was selected and tested for growth in hexadecane and for its ability to produce emulsifier. A culture of this strain, designated SB-30, has been deposited in the American Type Culture Collection, Washington, D.C., as *P.aeruginosa* A.T.C.C. 39615.

Although strains SB-1 and SB-30 both grow on liquid and solid paraffins and produce emulsifier in so doing, the strains are not identical. Morphologically, SB-1 is rough and nonmucoid, while strain SB-30 is smooth and mucoid. In addition, whereas SB-1 can grow on decane, SB-30 cannot do so.

Production of Emulsifier During Growth Of P.aeruginosa SB-1 or SB-30

The growth of P.aeruginosa SB-1 or SB-30 in a hydrocarbon containing medium is accompanied with the production of an emulsifying agent (EM). Initially, the emulsifier remains primarily bound with the cells, but is gradually released into the medium. It can be conveniently extracted from the medium with a conventional lipid-extracting solvent or solvent mixture, such as chloroform or chloroform-methanol (2:1), indicating that the emulsifier is lipid in nature. By evaporation of the solvent and drying under nitrogen, the crude emulsifier is recovered as a brown-yellow pasty liquid having surface active and emulsifying properties.

Alternatively, the emulsifier can be isolated by filtration through a porous membrane followed by adsorption on hydrophobic beads and solvent extraction. The culture is passed through 0.45 μm pellicon cassette filter (Millipore). In case of cultures grown in glucose the emulsifier passes through the filter and the cells are left behind in the retentate. The filtrate in this case is again filtered through a 10,000 dalton cut off filter, leaving the emulsifier in the retentate. The retentate is more than 10-fold concentrated compared with the original culture solution. The concentration effect can be enhanced if larger culture volumes are used. In case of chicken fat or corn oil cultures, the emulsifier (approximately 90%) remains associated with the cells collected by the 0.5 μm filter. The cells are then removed by centrifugation of the retentate.

The emulsifier from the concentrated cultures can be recovered by two methods, (1) by conventional solvent extraction or (2) by adsorption with hydrophobic beads, e.g., Adsorbosil-LC (silica gel beads with C-18 compound bonded to them, Applied Sciences, Milton Roy Company). One gm of beads adsorbs about 13,000 units of emulsifier from chicken fat culture. The beads are separated from the cultures by centrifugation and the emulsifier is extracted with chloroform-methanol (2:1). The beads can be reused indefinitely. This method gives a somewhat purer preparation.

Thin layer chromatography of the emulsifier on silica gel plates developed with a solvent system of chloroform-methanol-ammonium hydroxide (100:25:2.5) showed 5 or 6 major components, as detected by iodine staining. The emulsifiers isolated from both glucose and hexadecane-grown cultures of SB-1 or SB-30 show identical patterns in thin layer chromatography.

The activity of the crude emulsifier is not affected by proteinase or pronase, indicating that the emulsifier contains no protein. Similarly, the activity is not effected by DNase or RNase indicating that the emulsifier contains no nucleic acids. The crude emulsifier shows a positive reaction in an anthrone test, indicating the presence of carbohydrate. The positive anthrone test combined with the solubility of the emulsifier in chloroform-methanol indicates that the emulsifier is probably a glyco-lipid consisting of a lipid moiety and a polysaccharide (sugar moiety). The emulsifier is stable at room temperature and is not inactivated if autoclaved or dialyzed.

Figure 5B:
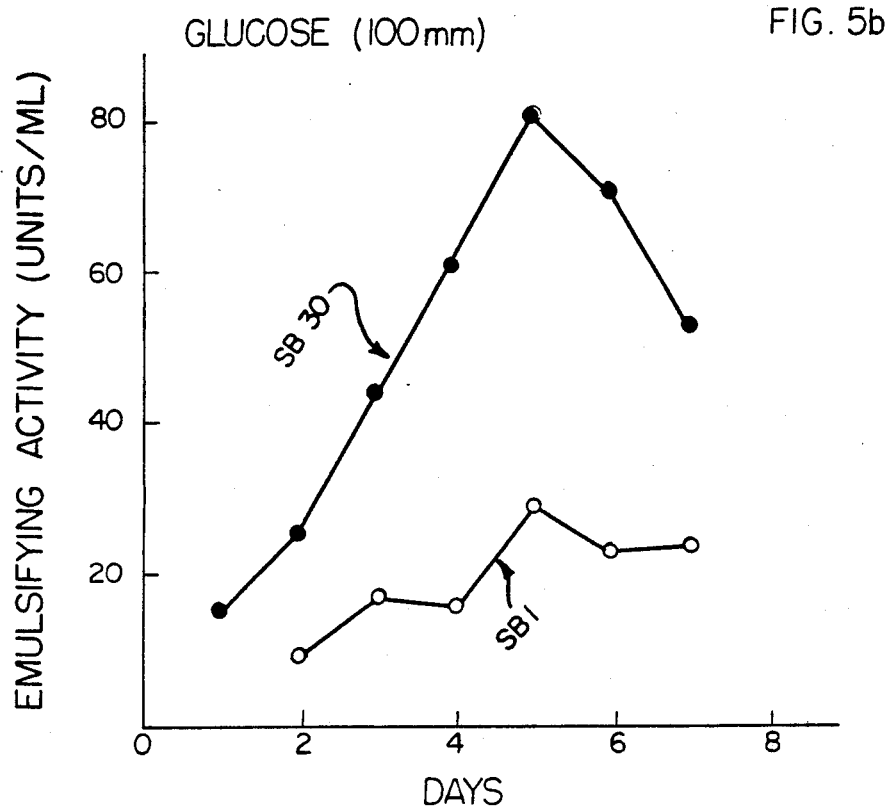
Figure 5C:
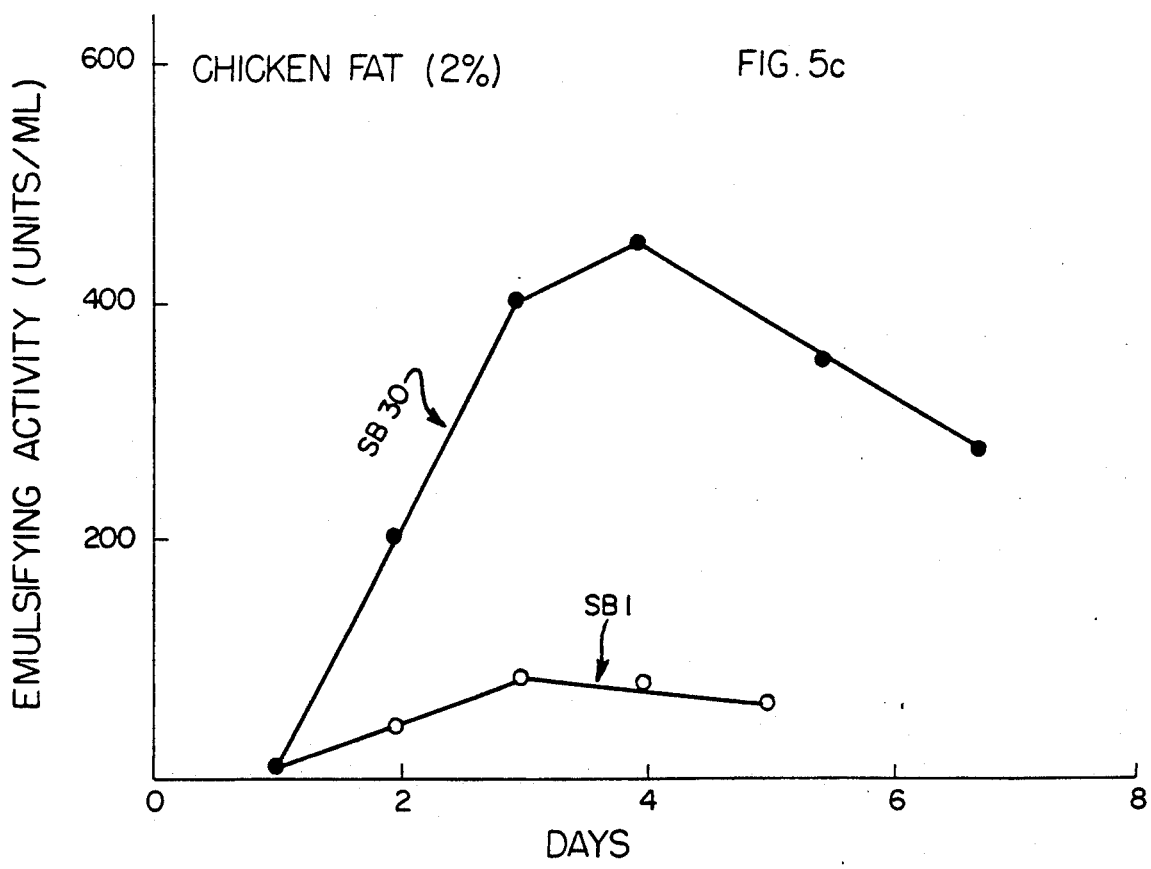

Strains SB-1 and SB-30 differ in their ability to produce emulsifier from different sources of carbon. As depicted in FIGS. 5a-c, although when grown on hexadecane (FIG. 5a), SB-1 and SB-30 produce approximately equivalent amounts of emulsifier, SB-30 produces about 2 to 3 times as much emulsifier as SB-1 when grown on glucose (FIG. 5b) or chicken fat (FIG. 5c), thus permitting this strain to be grown for the production of emulsifier on relatively cheap and available sources of carbon.

The data depicted in FIGS. 5a-c were obtained as follows. SB-1 and SB-30 were grown overnight in Luria broth, washed and resuspended in basal salt medium (BSM). An aliquot of each was inoculated to a 250 ml flask containing 50 ml BSM and a carbon source. The cultures were incubated with shaking at 30° C. At the indicated times, 1 ml of the culture was centrifuged and an aliquot of the supernatant was used for assay of the emulsifier. The emulsifier was assayed by vortexing for 1 minute a mixture of 5 ml of Tris-HCl buffer (20 mM, pH 8.0, containing 10 mM $MgCl_2$) and 0.1 ml of hexadecane-2-methyl naphthalene (1:1) with the emulsifier. The turbidity is read after 15 min. at room temperature. One unit of emulsifier is that amount that gives a reading of 100 in a Klett Summerson colorimeter using the red filter. The carbon sources in FIGS. 5a, 5b and 5c were (a) 2% hexadecane, (b) 100 mM glucose, and (c) 2% chicken fat.

FIG. 6 summarizes the data of FIGS. 5a-5c for the production of emulsifier by SB-30. As can be seen, SB-30 is very effective in producing emulsifier when grown on relatively inexpensive and available sources of carbon, such as corn oil and chicken fat, thus eliminating the necessity for using a relatively valuable substrate such as hexadecane. Other readily available sources of carbon, such as whey, cornsteep liquor and molasses can also be used.

Emulsifying Properties of Emulsifier Produced By SB-1 and SB-30

The biodegradable emulsifier produced by strains SB-1 and SB-30, is very effective for emulsifying a variety of organic substances in reducing the surface tension of water.

When the crude emulsifier in water is added to shale oil and shaken with a vortex mixer the shale oil is emulsified and its viscosity is reduced to a great extent. In addition, any oil clinging to the walls of the container is effectively removed and suspended, thus indicating the utility of the emulsifier for such uses as removal or recovery of oil from hard surfaces such as ballast tanks, barrels or drums or for the removal of oil sticking to solids such as rocks, sand, plastic materials and the like.

Table 1 illustrates the ability of the emulsifier to produce oil-in-water emulsions with organic solvents. The data of Table 1 were obtained by adding 300 μg of crude emulsifier and 0.1 ml of solvent to 7.5 ml of Tris buffer (0.02M Tris, pH 8.0, containing 0.01M $MgCl_2$), vortexing the mixture for 2 minutes, and transferring to 13 × 100 mm screw capped tubes. Readings were taken by a Spectronic 20 spectrophotometer at 540 nm and substracted from blanks containing no emulsifier.

As shown in Table 1, the emulsifier was effective in emulsifying a wide variety of organic materials. The emulsion produced with the aromatic solvents (toluene, benzene and xylene) was particularly dense and stable.

TABLE I

EMULSIFICATION OF ORGANIC SOLVENTS INTO WATER BY SB-1 EMULSIFIER

| Solvents | Absorbance of 540 nm at Different Times after Emulsification | | | | |
|---|---|---|---|---|---|
| | 30 min. | 2 hrs | 4 hrs. | 8 hrs. | 22 hrs. |
| Hexane | 0.05 | 0.05 | 0.04 | 0.03 | 0.025 |
| Octane | 0.17 | 0.06 | 0.04 | 0.02 | 0.015 |
| Decane | 0.445 | 0.205 | 0.137 | 0.075 | 0.035 |
| Undecane | 0.35 | 0.36 | 0.153 | 0.11 | 0.055 |
| Pentadecane | 0.295 | 0.235 | 0.155 | 0.045 | 0.036 |
| Hexadecane | 0.60 | 0.355 | 0.145 | 0.12 | 0.065 |
| Benzene | 1.5 | 1.45 | 1.45 | 1.3 | 1.26 |
| Toluene | 1.5 | 1.5 | 1.47 | 1.15 | 1.02 |
| Xylene | 2.0 | 1.46 | 1.37 | 1.32 | 1.02 |
| Chloroform | 1.36 | 1.24 | 1.12 | 1.07 | 1.0 |
| Petroleum ether | 0.22 | 0.04 | — | — | — |

The emulsifier produced in accordance with the invention is also effective in emulsifying heavy oil such as shale oil. This ability was demonstrated by adding 2 ml of shale oil, 5 ml of tap water and 700 μg of emulsifier to a tube and vortexing for 2 min. After a period of 15 min. at room temperature, the emulsion had not broken. By comparison, a control sample containing no emulsifier had separated into 2 distinct phases.

The surfactant properties of the emulsifier produced in accordance with the invention are demonstrated by the data of Table 2. In the work summarized in the Table, emulsifier produced by strains SB-1 and SB-30 during growth on different substrates was added to water in the relative amounts indicated, and the surface tension of the water was measured. It will be seen that the emulsifier produced by strain SB-30 is more efficient than that produced by SB-1, even when the same substrates are used.

TABLE 2

Reduction of Surface Tension of Water By Emulsifier Produced by Growth of SB-1 and SB-30 On Different Substrates

| Strain | Carbon Source | Amount of Emulsifier (μL) | Surface Tension of Water (DYNES/Cm) |
|---|---|---|---|
| — | — | — | 74 |
| SB-1 | Hexadecane | 20 | 40 |
| SB-1 | Glucose | 30 | 51 |
| SB-30 | Glucose | 1 | 35 |
| SB-30 | Hexadecane | 1 | 31 |
| SB-30 | Luria broth (LB) | 5 | 46 |
| SB-30 | Dodecane | 5 | 28.5 |
| SB-30 | Succinate | 5 | 37 |
| SB-30 | Tetradecane | 5 | 31 |
| SB-30 | Tetracosane | 5 | 27 |
| SB-30 | LB + Hexadecane | 5 | 32 |

The foregoing detailed description has been given for clearness of understanding only, and no unnecessary limitations should be understood therefrom as modifications will be obvious to those skilled in the art.

What is claimed is:

1. A biologically pure culture of *Pseudomonas aeruginosa* SB-30, A.T.C.C. 39615 capable of utilizing paraffins having no less than 12 carbon atoms as a source of carbon and energy.

2. A method for producing a lipid composition having emulsifying and surface active properties which comprises growing the bacteria of claim 1 an aqueous nutrient medium including a source of carbon, separating the bacteria from the medium, and recovering said composition from said medium.

3. The method of claim 2 wherein said composition is recovered by solvent extraction of said medium with a lipid-extracting solvent.

4. The method of claim 3 wherein said solvent is chloroform or a chloroform-methanol mixture.

* * * * *